United States Patent [19]

Poss

[11] Patent Number: 5,035,740
[45] Date of Patent: Jul. 30, 1991

[54] HERBICIDAL COMPOUNDS

[75] Inventor: Kathleen M. Poss, Lawrenceville, N.J.

[73] Assignee: FMC Corporation, Philadelphia, Pa.

[21] Appl. No.: 352,794

[22] Filed: May 16, 1989

[51] Int. Cl.$^5$ .................. C07D 253/06; A01N 43/707
[52] U.S. Cl. .......................................... 71/93; 544/182
[58] Field of Search .............................. 544/182; 71/93

[56] References Cited

U.S. PATENT DOCUMENTS

| 4,318,731 | 3/1982 | Kajioka et al. | 71/92 |
| 4,439,229 | 3/1984 | Swithenbank | 71/96 |

FOREIGN PATENT DOCUMENTS

| 0011693 | 6/1980 | European Pat. Off. |
| 0275131 | 7/1988 | European Pat. Off. |
| 0300387 | 1/1989 | European Pat. Off. |
| 0300398 | 1/1989 | European Pat. Off. |
| 3603789 | 8/1987 | Fed. Rep. of Germany |
| 56-53662 | 5/1981 | Japan |
| 58-225070 | 12/1983 | Japan |

OTHER PUBLICATIONS

PCT International Application No. WO 87/07602, Published Dec. 17, 1987.
PCT International Application No. 86/04481, published Aug. 14, 1986.
PCT International Application No. WO 85/01939, published May 19, 1985.

Primary Examiner—John M. Ford
Attorney, Agent, or Firm—Stanford M. Back; Robert M. Kennedy

[57] ABSTRACT

A herbicidal compound of the formula

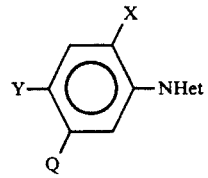

in which

Q is $-CR^1(R^2)C(R^3)(R_4)Q'$ or $-CR^1=C(R^4)Q'$;
$R^1$, $R^2$ and $R^3$ are each, independently, hydrogen, halogen, or lower alkyl;
$R^4$ is hydrogen or lower alkyl;
Q' is COOH, COOZ, COOR$^5$, CON (R$^6$)(R$^7$), CN, CHO or C(O)R$^5$;
Z is a salt-forming cation;
R$^5$ is alkyl, cycloalkyl or aralkyl;
each of R$^6$ and R$^7$ is, independently, hydrogen alkyl, cycloalkyl, alkenyl, alkynyl, alkoxy, phenyl, benzyl, or SO$_2$R$^8$ or is one of said radicals substituted by halogen, alkyl, or cyano, R$^8$ being the same as R$^6$ other than hydrogen or SO$_2$R$^8$;
NHet is a monovalent nitrogen-containing organic group; and
NHet, X and Y are such that the Methoxy Analog or Propargyloxy Analog of said compound is a herbicide.

30 Claims, No Drawings

HERBICIDAL COMPOUNDS

This invention relates to novel herbicides for weed control in agriculture, horticulture and other fields where it is desired to control unwanted plant growth, such as grassy or broadleaf plant species. The invention also relates to intermediates for the production of such herbicides.

One aspect of this invention relates to herbicidal compounds of the formula

Q-Ar-NHet   Formula I where Q-Ar is a substituted phenyl radical (e.g. of the formula

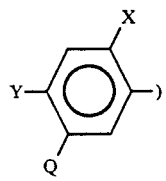

in which the substituent Q is at the 5-position (meta to the nitrogen of said formula I); and where Q is a group of the formula:
—$CR^1(R^2)C(R^3)(R^4)Q'$ or —$CR^1$=$C(R^4)Q'$ in which Q' is a carboxylic acid group (i.e. COOH) or a salt, ester, amide, or nitrile of such carboxylic acid group. Thus Q' may be:
$CO_2H$,
$CO_2Z$,
$CO_2R^5$,
$CON(R^6)(R^7)$, or
CN.

In another aspect of this invention Q' may be an aldehydic or ketonic group, e.g. —CHO or —$COR^5$.

Z may be a salt-forming cation, such as one which forms a base addition salt with a carboxylic acid (e.g., a sodium, potassium, calcium, ammonium, magnesium, or mono-, di- or tri($C_{1-4}$ alkyl)ammonium or sulfonium or sulfoxonium ion). $R^5$ may be alkyl, cycloalkyl of 3 to 6 carbon atoms (e.g. cyclopropyl or cyclopentyl), or aralkyl such as benzyl or substituted benzyl (e.g., halobenzyl, alkylbenzyl, or haloalkylbenzyl, such as 4-chlorobenzyl or 4-trifluoromethylbenzyl). $R^6$ and $R^7$ may each, independently, be hydrogen, hydroxy, alkyl, cycloalkyl, alkenyl, alkynyl (e.g., propynyl), alkoxy, phenyl, benzyl, or $SO_2R^8$ in which $R^8$ is the same as $R^6$ other than hydrogen or $SO_2R^8$, or any of the foregoing carrying additional substituents; such additional substituents may be halogen, haloalkyl (e.g. chloroethyl), halophenyl (e.g. chlorophenyl), or halobenzyl (e.g. chlorobenzyl); alkyl; or cyano.

In the foregoing formula for Q, $R^1$, $R^2$ and $R^3$ may each, independently, be hydrogen, alkyl such as lower alkyl (e.g. methyl) or halogen such as chlorine, bromine, or fluorine, while $R^4$ may be hydrogen or lower alkyl.

In Formula I above Ar and NHet are so chosen that when Q is methoxy or propargyloxy (instead of Q having the formula given above) the compound is a herbicide. Compounds in which Q in Formula I is methoxy or propargyloxy are, for convenience, here designated as Methoxy Analogs and the Propargyloxy Analogs of the claimed novel compounds. Such Methoxy Analogs and Propargyloxy Analogs are well known in the art.

Preferably, "Ar" carries a substituent (i.e. other than hydrogen) at the 2-position or the 4-position of the phenyl radical, most preferably at both the 2-and 4-positions.

X may be hydrogen; halogen such as chlorine, bromine, or fluorine (preferably fluorine or chlorine); alkyl such as lower alkyl (e.g. methyl); haloalkyl such as halo lower alkyl (e.g. $CF_3$, $CH_2F$ or $CHF_2$); alkoxy such as lower alkoxy (e.g. methoxy); or $NO_2$; and Y may be hydrogen; halogen such as chlorine, bromine, or fluorine (preferably bromine or chlorine); alkyl such as lower alkyl (e.g. methyl); alkoxy such as lower alkoxy (e.g. methoxy); alkylthio such as lower alkylthio (e.g. methylthio); haloalkyl such as halo lower alkyl (e.g. fluoroalkyl); halo lower alkylsulfinyl (e.g. —$SOCF_3$); or haloalkoxy such as halo lower alkoxy (e.g. as —$OCHF_2$).

Presently preferred X and Y substituents are: 2-F, 4-Cl; 2-F, 4-Br; 2,4-$Cl_2$; 2-Br, 4-Cl; and 2-F,4-$CF_3$.

In the preferred compounds of this invention, NHet and Ar (or X and Y) are so chosen that the Methoxy Analog or the Propargyloxy Analog of such preferred compound has marked herbicidal properties, such Analog showing at least 50% kill of at least one of the following plant species when applied under at least one of the following modes at the rate of 0.5 kg/ha, and more preferably showing such 50% kill when applied at the rate of 0.1 kg/ha:

Species: velvetleaf (*Abutilon theophrasti*), green foxtail (*Setaria viridis*); Modes: pre-emergent, postemergent. Testing for such herbicidal activity may be carried out in the manner described below under the heading "Herbicidal Activity".

NHet is a monovalent nitrogen-containing organic group. NHet may be one of the following groups, for example:

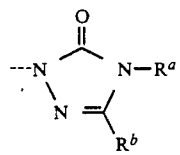

where $R^a$ and $R^b$ are, for example, independently, alkyl or haloalkyl or other radicals such as those disclosed in U.S. Pat. Nos. 4,318,731; 4,398,943; 4,404,019; 4,743,291; 4,702,945; 4,705,557; 4,702,763; 4,761,174 and International patent publications WO 85/01637, WO 85/04307, WO 87/00730, WO 87/03782, WO 86/04481 and WO 88/01133;

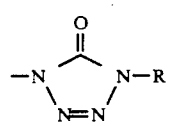

where R is, for example, alkyl or haloalkyl or other radical, such as those disclosed in U.S. Pat. No. 4,734,124 and International patent publications WO 85/01939 and WO 87/03873;

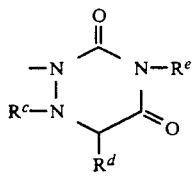

where $R^c$ and $R^d$ are each H or together constitute a double bond and $R^e$ is, for example, an alkyl, haloalkyl or other radical, such as those disclosed in U.S. Pat. Nos. 4,755,217 and 4,766,233 and International patent publication WO 86/00072;

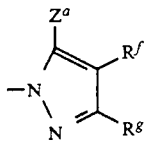

where $Z^a$ is halo, alkyl, alkoxy, alkylsulfonyl, etc., and $R^f$ and $R^g$ may be alkyl, or taken together may be alkylene for instance, such as disclosed in Derwent Abstracts accession nos. 84-090669 (British patent 2,127,410); 85-100678 (European patent 138,527); 86-04852 and 88-101642;

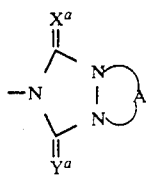

where, for instance, $X^a$ and $Y^a$ may be O or S and A may be $(CH_2)_n$ such as disclosed in Derwent Abstracts aCCession nos. 86-133831, 87-215141 (European patent 230,874) and 86-140810;

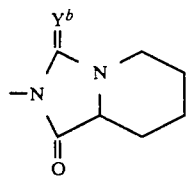

where $Y^b$ may be O or S, such as disclosed in Derwent Abstracts accession nos. 85-240363 and 87-21541;

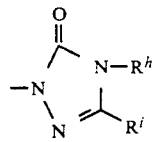

where, for instance, $R^h$ and $R^i$ may together constitute an alkylene group, such as disclosed in Derwent Abstracts accession no. 86-133830;

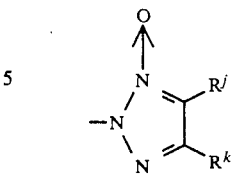

where, for instance, $R^j$ and $R^k$ together constitute an alkylene group, such as disclosed in Derwent Abstracts accession nos. 88-191726, 88-163183 and 88-243443;

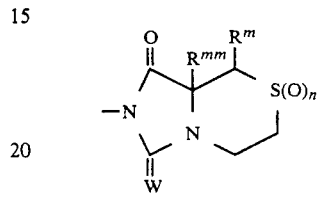

where, for instance, n is 0, 1, or 2; W is O or S; and $R^{mm}$ and $R^m$ may be H; or $R^{mm}$ may be Cl and $R^m$ may be H; or $R^{mm}$ and $R^m$ together form a double bond such as disclosed in U.S. Pat. No. 4,179,276 and Derwent Abstracts accession nos. 88-163183 and 88-243443;

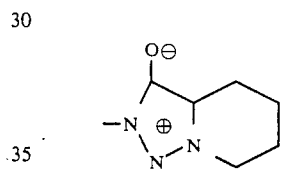

such as disclosed in Derwent Abstracts accession nos. 84-214701, 88-163183 and 88-243443;

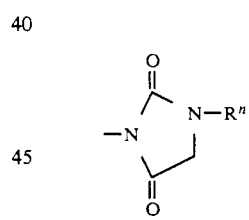

where, for instance, $R^n$ is lower alkyl, alkenyl, alkynyl or cycloalkyl such as disclosed in European patent 69855 and Derwent Abstracts accession no. 84-027480;

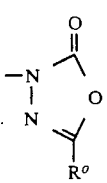

where $R^o$ is lower alkyl or cycloalkyl such as disclosed in Derwent Abstracts accession nos. 84-246947, 87-238787 or 88-190606 (International patent publication WO 8804653) and U.S. Patent Nos. 3,385,862; 3,836,539; and 3,876,413;

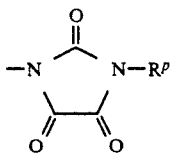

where $R^p$ is, for instance, lower alkyl, e.g., isopropyl;

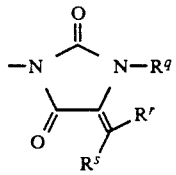

where, for example, $R^q$ is H, alkyl, alkenyl or alkynyl and $R^r$ and $R^s$ are H or lower alkyl, such as disclosed in Derwent Abstracts accession no. 88-092987 (European patent 262428);

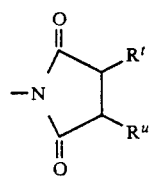

where, for example, $R^t$ is hydrocarbyl group such as propyl, and $R^u$ may be H or hydroxycarbonyl, such as disclosed in Derwent Abstracts accession nos. 88-168716 (German patent 3636552) and 88-243443;

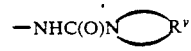

where $R^v$ is alkylene which may be substituted, such as disclosed in Derwent Abstracts accession nos. 84-034261 and 84-090045;

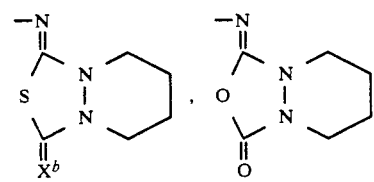

where $X^b$ is O or S, such as disclosed in Derwent Abstracts accession no. 87-040749;

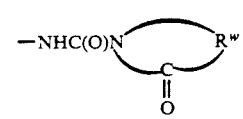

where $R^w$ is, for example, alkylene such as tetramethylene;

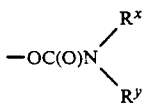

where $R^x$ and $R^y$ may together constitute an alkylene group which may be interrupted by O, S or vinylene, such as disclosed in U.S. Pat. No. 4,521,242 and Derwent Abstracts accession no. 86-180564.

U.S. Pat. No. 4,439,229 and International patent publication WO 87/07602 also disclose other NHet rings which may be used, such rings being illustrated, for example, at column 4 line 25 to column 5 line 20 of U.S. Pat. No. 4,439,229 and at pages 12 to 14 of WO 87/07602. It will be seen that many of the suitable NHet groups comprise a 5- or 6-membered heterocyclic ring having one to four ring-nitrogen atoms and having the formula

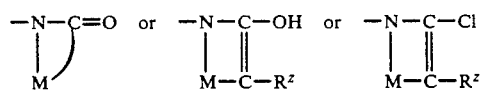

where M represents the balance of the heterocyclic ring and $R^z$ represents hydrogen or a substituent group.

Particularly suitable compounds are those whose Methoxy Analog or Propargyloxy Analog, e.g., an Analog of the formula

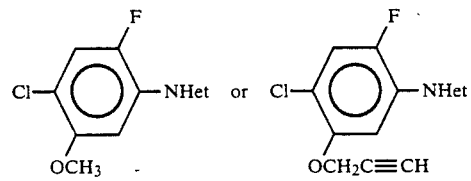

is a plant-membrane disrupting herbicide which acts as an inhibitor of the enzyme protoporphyrinogen oxidase, its $I_{50}$ for that enzyme being less than 1 $\mu$M preferably less than about 0.3 $\mu$M, e.g. an $I_{50}$ of about 0.1 or 0.03 or 0.01 $\mu$M or less. A test for such inhibition is set forth in Appendix C below.

One test for the membrane (plasmalemma) disruption capacity is the Efflux Experiment described in the article by Halling and Peters in *Plant Physiology*, 84, 1114–5 (1987). In such a test (described in more detail in Appendix A below), the Methoxy or Propargyloxy analog preferably shows a total efflux of at least 50% at a treatment rate of 100 $\mu$M, preferably at a treatment rate of 1 $\mu$M or less, such as 100 nM; highly active materials, such as 1-(4-chloro-2-fluoro-5-propargyloxyphenyl)-3-methyl-4-difluoromethyl-$\Delta^2$-1,2,4-triazolin-5-one, give total efflux percentages of over 90% at 100 nM concentration.

Another test of the capacity of a material for disrupting the plasmalemma of plant material is the Light-Induced Greening Inhibition Test described more particularly in Appendix B below. This test measures the capacity to inhibit the light-greening of dark-bleached *Chlamydomonas reinhardi* mutant y-1 (a type of algae which when grown in the dark does not make chlorophyll, so that the mass of algae becomes bleached owing to the presence of new non-green cells, and which produces chlorophyll again when it is exposed to light). The compounds of this invention preferably are those whose Methoxy or Propargyloxy analog has the ability to inhibit the light-greening by at least 50% when used at a concentration of $10^{-5}$M, more preferably at a concentration of $10^{-6}$M or less, e.g., $10^{-7}$M. In addition, the compound should be one whose Methoxy or Propargyloxy Analog, when used at said concentration in the Light-Greening Inhibition Test, gives a supernatant which shows a light absorption peak at about 405 nm which is higher than the chlorophyll peak (the peak at about 668 nm in this system), e.g. the supernatant shows a 405 nm peak whose height is 2, 3 or 4 times the height of the 668 nm peak.

Representative compounds of this invention are listed in Table 1 below.

One may describe many of the compounds of this invention by the formulas

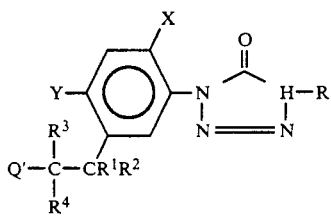

Formula Ia

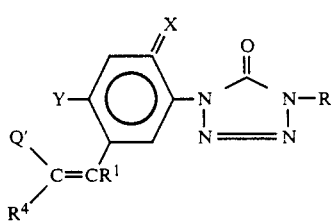

Formula II in which Q', $R^1$, $R^2$, $R^3$ and $R^4$ have the meanings set forth above and the substituent $R^1$ on the tetrazolinone ring may be any of those known in the prior art discussed above.

X may be hydrogen; halogen such as chlorine, bromine, or fluorine (preferably fluorine or chlorine); alkyl such as lower alkyl (e.g. methyl); haloalkyl such as halo lower alkyl (e.g., $CF_3$, $CH_2F$ or $CHF_2$); alkoxy such as lower alkoxy (e.g., methoxy); or nitro; and Y may be hydrogen; halogen such as chlorine, bromine, or fluorine (preferably bromine or chlorine); alkyl such as lower alkyl (e.g. methyl); alkoxy such as lower alkoxy (e.g. methoxy); haloalkyl such as halo lower alkyl (e.g. fluoroalkyl); alkylthio such lower alkylthio (e.g. methylthio); halo lower alkylsulfinyl (e.g., —SOCF$_3$); or halo lower alkoxy (e.g., —OCHF$_2$).

Presently preferred X and Y substituents are 2-F, 4-Cl; 2-F, 4-Br; 2,4-Cl$_2$; 2-Br, 4-Cl; and 2-F, 4-CF$_3$.

In each aspect of the invention it is often preferable that any alkyl, alkenyl, alkynyl or alkylene moiety (such as the hydrocarbon moiety of an alkoxy or haloalkoxy group) has up to about 6 carbon atoms, e.g., 1 to 4 or 5 carbon atoms, and that any cycloalkyl moiety have 3 to 7 ring carbon atoms, more preferably 3 to 6 carbon atoms.

Any acidic compound of this invention, including sulfonamides in which NR$^6$R$^7$ is NHSO$_2$R$^8$, may be converted to the corresponding base addition salt, such as a salt in which the salt-forming cation is Z (Z being as described above).

The present compounds may be prepared by methods described in the literature or in the following Examples or by methods analogous and similar thereto and within the skill of the art. In the Example below a compound of the formula

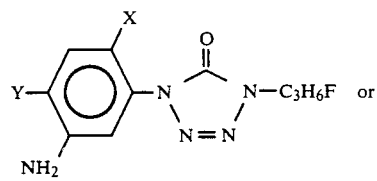

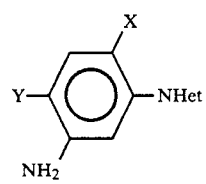

(such as the compound shown in Example 1E of International patent publication WO/03873, published July 2, 1987, in which X=F, Y=Cl and R=—(CH$_2$)$_3$F) is reacted (according to a procedure described by Doyle et al., J. Org. Chem. 42, 2431 (1977)) with an alkyl nitrite, a copper (II) halide, and an olefinic compound having the formula C(R$^1$)(R$^2$)=C(R$^4$)Q' to form a compound of formula I above in which Q is —C(R$^1$)(R$^2$)C(R$^3$)(R$^4$)Q' and in which R$^3$ is halogen and R$^2$ is hydrogen. That compound may be dehydrohalogenated (e.g., with sodium hydride or other suitable base) to yield a compound of formula II above in which Q is —C(R$^1$)=C(R$^4$)Q'. To produce the latter, one may also use the method of Example 1 below starting with a compound of the formula

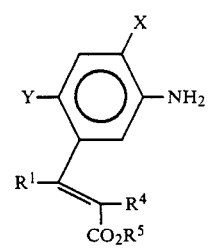

such as the 3-amino-6-chloro-4-fluorocinnamic acid ethyl ester described in Japanese published application 59-15538 of Sep. 4, 1984. The amino group is converted to an NHet group, as by a method described in the above-mentioned International patent publication WO 85/01939 forming a compound of the formula

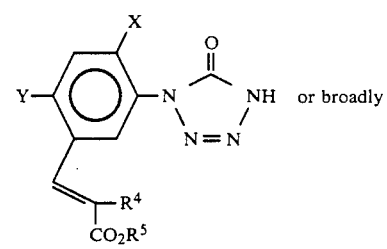

or broadly

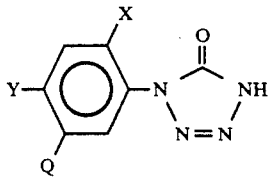

The reactant $C(R^1)R^2=C(R^4)Q'$ may be, for example, methyl acrylate, ethyl acrylate, methyl methacrylate, methyl 3-chloroacrylate, methacrolein, vinyl methyl ketone, ethyl crotonate, acrylonitrile, methacrylonitrile or the like.

The $-C(R^1)=C(R^4)CO_2R^5$ group may be hydrogenated or halogenated to form a compound in which Q is $-C(R^1)(R^2)C(R^3)(R^4)Q'$ and $R^2$ and $R^3$ are hydrogen (from hydrogenation as in Example 1D below) or $R^2$ and $R^3$ are halogen (from halogenation as in Example 2). When Q' is $CO_2H$, the acidic compound of formula I may be converted to the corresponding amide, such as by first treating with a reagent such as thionyl chloride to form the acid halide (wherein Q' is, for example, —COCl) and then reacting with ammonia or an amine. Alternative methods of amide formation may involve known carbodiimidemediated coupling.

The invention is illustrated further in the following Examples. In this application all temperatures are in °C. unless otherwise indicated.

EXAMPLE 1

Ethyl 3-[2-Chloro-4-fluoro-5-[4-(3-fluoropropyl)-1,4-dihydro-5-oxo-5H-tetrazol-1-yl]phenyl]propionate Step A Ethyl 3-[2-chloro-4-fluoro-5-(1,4-dihydro-5-oxo-5H-tetrazol-1-yl)phenyl]-propenoate A stirred mixture of 8.06 g (0.0449 mole) of ethyl 3-(5-amino-2-chloro-4-fluorophenyl)propenoate and 5.32 g (0.0269 mole) of trichloromethyl chloroformate in 200 mL of 1,4-dioxane was heated at reflux for approximately three hours. The solvent was removed by distillation under reduced pressure, leaving a residue. To this residue was added 50 mL of trimethylsilyl azide, and the resultant mixture was stirred and heated at reflux for approximately 18 hours. The mixture was cooled and was diluted with toluene. The organic mixture was washed with water. The organic phase was evaporated under reduced pressure, leaving a residue. This residue was dissolved in ethyl acetate and was washed in succession with 1N hydrochloric acid, an aqueous, saturated sodium bicarbonate solution, and water. The washed organic phase was dried over anhydrous magnesium sulfate and was filtered. The filtrate was evaporated under reduced pressure leaving a residue. This residue was purified by column chromatography on silica gel to yield ethyl 3-[2=chloro-4-fluoro-5-(1,4-dihydro-5-oxo-5H-tetrazol-1-yl)phenyl]propenoate as a solid, mp 106°-109° C.

The ir and nmr spectra were consistent with the proposed structure.

Step B 3-Fluoropropyl methanesulfonate

To an ice cold, stirred solution of 19.0 g (0.244 mole) of 3-fluoropropanol and 39.5 g (0.300 mole) of triethylamine in 300 mL of methylene chloride was added dropwise 34.4 g (0.300 mole) of methanesulfonyl chloride. The resultant mixture was allowed to warm to room temperature and was stirred for approximately 18 hours. The mixture was poured into water and was washed with an aqueous, saturated sodium bicarbonate solution. The organic phase was dried over anhydrous magnesium sulfate and was filtered. The filtrate was distilled under reduced pressure to yield 41.3 g of 3-fluoropropyl methanesulfonate as a liquid, bp 116° C./15 mm Hg.

The nmr spectrum was consistent with the proposed structure.

Step C Ethyl 3-[2-chloro-4-fluoro-5-[4-(3-fluoropropyl)-1,4-dihydro-5-oxo-5H-tetrazol-1-yl]phenyl]propenoate To a stirred mixture of 2.62 g (0.00830 mole) of ethyl 3-[2-chloro-4-fluoro-5-(1,4-dihydro-5-oxo-5H-tetrazol-1-yl)phenyl]propenoate in 20 mL of N,N-dimethylformamide was added 1.46 g (0.00939 mole) of 3-fluoropropyl methanesulfonate and 1.30 g (0.00939 mole) of potassium carbonate. The reaction mixture was heated at 50°-60° C. and was stirred at that temperature for approximately 18 hours. The mixture was cooled and was poured into ice water. This mixture was extracted with ethyl acetate. The extract was dried over anhydrous magnesium sulfate and was filtered. The filtrate was evaporated under reduced pressure to yield 0.76 g of ethyl 3-[2-chloro-4-fluoro-5-[4-(3-fluoropropyl)-1,4-dihydro-5-oxo-5H-tetrazol-1-yl]phenyl]propenoate as an oil, compound 4 of Table 1.

The nmr spectrum was consistent with the proposed structure.

Step D Ethyl 3-[2-chloro-4-fluoro-5-[4-(3-fluoropropyl)-1,4-dihydro-5-oxo-5H-tetrazol-1-yl]phenyl]propionate The hydrogenation of 0.45 g (0.0012 mole) of ethyl 3-[2-chloro-4-fluoro-5-[4-(3-fluoropropyl)-1,4-dihydro-5-oxo-5H-tetrazol-1-yl]phenyl]propenoate with approximately 0.1 g of platinum (IV) oxide in ethyl acetate yielded 0.43 g of ethyl 3-[2-chloro-4-fluoro-5[4-(3-fluoropropyl)-1,4-dihydro-5-oxo-5-H-tetrazol-1-yl]phenyl]propionate as an oil, compound 1 of Table 1.

The nmr and ir spectra were consistent with the proposed structure.

EXAMPLE 2

Ethyl 2,3-Dibromo-3-[2-chloro-4-fluoro-5-[4-(3-fluoropropyl)-1,4-dihydro-5-oxo-5H-tetrazol-1-yl]phenyl]propionate The bromination of 0.34 g (0.00091 mole) of ethyl 3-[2-chloro-4-fluoro-5-[4-(3-fluoropropyl)-1,4-dihydro-5-oxo-5H-tetrazol-1-yl]phenyl]propenoate with five drops of bromine in 10 mL of methylene chloride yielded 0.38 g of ethyl 2,3-dibromo-3-[2-chloro-4-fluoro-5-[4-(3-fluoropropyl)-1,4-dihydro-5-oxo-5H-tetrazol-1yl]phenyl]propionate as an oil, compound 2 of Table 1.

The nmr and ir spectra were consistent with the proposed structure.

EXAMPLE 3

Ethyl 2-chloro-3-[2-chloro-4-fluoro-5-[4-(3-fluoropropyl)-1,4-dihydro-5-oxo-5H-tetrazol-1-yl]phenyl]propionate To an ice cold, stirred mixture of 5.54 g (0.0553 mole) of ethyl acrylate, 10 mL of acetonitrile, 0.43 g (0.0042 mole) of tert-butyl nitrite, and 0.45 g (0.0033 mole) of copper (II) chloride was added a solution of 0.80 g (0.0028 mole) of 1-(5-amino-4-chloro-2-fluorophenyl)-1,4-dihydro-4-(3-fluoropropyl)-5H-tetrazol-5-one (which may be prepared as described in International patent publication WO 87/03873, Example 1 A–E) in 10 mL of acetonitrile. The reaction mixture was stirred at room temperature for five hours and then was diluted with 2N hydrochloric acid. The acidic mixture was extracted with three portions of diethyl ether. The extracts were combined and dried over anhydrous magnesium sulfate. The dried organic phase was filtered and the filtrate was evaporated leaving a residue. This residue was purified by column chromatography on silica gel, eluting with n-heptane: ethyl acetate (2:1) to yield 1.1 g of ethyl 2-chloro-3-[2-chloro-4-fluoro-5-[4-(3-fluoropropyl)-1,4-dihydro-5-oxo-5H-tetrazol-1-yl]phenyl]propionate as an oil, compound 3 of Table 1.

The nmr spectrum was consistent with the proposed structure.

EXAMPLE 4

Methyl 3-[2,4-dichloro-5-(4-difluoromethyl-4,5-dihydro-3-methyl-5-oxo-1H-1,2,4-triazol-1-yl)phenyl]propionate Step A Methyl 2-Chloro-3-[2,4-dichloro-5-(4-difluoromethyl-4,5-dihydro-3-methyl-5-oxo-1H-1,2,4-triazol-1-yl)phenyl]propionate To a cold (0° C.), stirred mixture of 28.7 g (0.333 mole) of methyl acrylate, 2.51 g (0.0244 mole) of tert-butyl nitrite, and 2.6 g (0.019 mole) of copper (II) chloride in 50 mL of acetonitrile was added dropwise a solution of 5.0 g (0.016 mole) of 1-(5-amino-2,4-dichlorophenyl)-4-difluoromethyl-4,5-dihydro-3-methyl-1,2,4-triazol-5(1H)-one in 15 mL of acetonitrile. After complete addition the reaction mixture was allowed to war to room temperature and was stirred for approximately 18 hours. The reaction mixture was diluted with 15 mL of 2N hydrochloric acid solution. The mixture was extracted with four portions of diethyl ether. The combined extracts were dried over anhydrous magnesium sulfate, filtered, and the filtrate evaporated under reduced pressure to give an oil. The oil was purified by column chromatography on silica gel, eluting with n-heptane:ethyl acetate (4:1) to give 5.0 g of methyl 2-chloro-3-[2,4-dichloro-5-(4-difluoromethyl-4,5-dihydro-3-methyl-5-oxo-1H-1,2,4-triazol-1-yl)phenyl]propionate as an oil, Compound A3 of Table 1A.

Step B Methyl 3-[2,4-dichloro-5-(4-difluoromethyl-4,5-dihydro-3-methyl-5-oxo-1H-1,2,4-triazol-1-yl)phenyl]propenoate To a stirred, cold (0° C.) solution of 4.16 g (0.0100 mole) of methyl 2-chloro-3-[2,4-dichloro-5-(4-difluoromethyl-4,5-dihydro-3-methyl-5-oxo-1H-1,2,4-triazol-1-yl)phenyl]propionate in 15 mL of N,N-dimethylformamide was added portionwise 0.29 g (0.012 mole) of sodium hydride. After complete addition the reaction mixture was allowed to warm to room temperature and was stirred for 30 minutes. The reaction mixture was heated at 60° C. for six hours and then was stirred at room temperature for approximately 18 hours. The reaction mixture was poured into ice water, and the resultant aqueous mixture was extracted with four portions of diethyl ether. The extracts were combined and washed successively with water and an aqueous, saturated sodium chloride solution. The washed organic phase was dried over anhydrous magnesium sulfate and was filtered. The filtrate was evaporated under reduced pressure to give a white foam. The foam was purified by column chromatography on silica gel, eluting with n-heptane:ethyl acetate (4:1), to give 1.63 g of methyl 3-[2,4-dichloro-5-(4-difluoromethyl-4,5-dihydro-3-methyl-5-oxo-1H-1,2,4-triazol-1-yl)phenyl]propenoate as a solid, m.p. 148°–151° C., Compound A39 of Table 1A.

Step C Methyl 3-[2,4-dichloro-5-(4-difluoromethyl-4,5-dihydro-3-methyl-5-oxo-1H-1,2,4-triazol-1-yl)phenyl]propionate Hydrogenation of 0.59 g (0.0016 mole) of methyl 3-[2,4-dichloro-5-(4-difluoromethyl-4,5-dihydro-3-methyl-5-oxo-1H-1,2,4-triazol-1-yl)phenyl]propenoate (Compound A39) over approximately 0.2 g (0.0009 mole) of platinum (IV) oxide in approximately 15 mL of ethyl acetate gave after filtration and concentration 0.59 g of methyl 3-[2,4-dichloro-5-(4-difluoromethyl-4,5-dihydro-3-methyl-5-oxo-1H-1,2,4-triazol-1-yl)phenyl]propionate as a clear oil, which crystallized upon standing. The crystals were triturated with petroleum ether and recovered by filtration, m.p. 70°–73° C., Compound A1 of Table 1A.

EXAMPLE 5

Methyl 2,3-dibromo-3-[2,4-dichloro-5-(4-difluoromethyl-4,5-dihydro-3-methyl-5-oxo-1H-1,2,4-triazol-1-yl)-phenyl]-propionate In a manner similar to that of Abbott and Althoresen, *Org. Syn.*, Coll. Vol. 2, pg 270, 0.24 g (0.00063 mole) of methyl 3-[2,4-dichloro-5-(4-difluoromethyl-4,5-dihydro-3-methyl-5-oxo-1H-1,2,4-triazol-1-yl)phenyl]propenoate (Compound A39) was treated with six drops of bromine in 15 mL of carbon tetrachloride to give 0.40 g of methyl 2,3-dibromo-3-[2,4-dichloro-5-(4-difluoromethyl-4,5-dihydro-3-methyl-5-oxo-1H-1,2,4-triazol-1-yl)phenyl]propionate as a solid, Compound A10 of Table 1A.

The nmr spectrum was consistent with the proposed structure.

EXAMPLE 6

N-Cyclopropyl-2-chloro-3-[2,4-dichloro-5-(4-difluoromethyl-4,5-dihydro-3-methyl-5-oxo-1H-1,2,4-triazol-1-yl)phenyl]propionamide Step A 2-Chloro-3-[2,4-dichloro-5-(4-difluoromethyl-4,5-dihydro-3-methyl-5-oxo-1H-1,2,4-triazol-1-yl)phenyl]propionic acid To a stirred mixture of 26.3 g (0.366 mole) of acrylic acid, 2.83 g (0.275 mole) of tert-butyl nitrite, and 2.94 g (0.0220 mole) of copper (II) chloride in 75 mL of acetonitrile was added slowly 5.65 g (0.0183 mole) of 1-(5-amino-2,4-dichlorophenyl)-4-difluoromethyl-4,5-dihydro-3-methyl-1,2,4-triazol-5(1H)-one. The reaction mixture was stirred at room temperature for three hours. The reaction mixture was poured into 2N hydrochloric acid solution, and the whole was extracted with diethyl ether. The organic phase was dried over anhydrous magnesium sulfate, filtered, and the filtrate evaporated under reduced pressure to give a yellow solid. The solid was triturated with water and was filtered. The filter cake was dried to give 5.9 g of 2-chloro-3-[2,4-dichloro-5-(4-difluoromethyl-4,5-dihydro-3-methyl-5-oxo-1H-1,2,4-triazol-2-yl)phenyl]propionic acid, Compound A2 of Table 1A.

The nmr spectrum was consistent with the proposed structure. A similarly prepared sample of Compound A2 had a melting point of 138°–141° C.

Step B  N-Cyclopropyl-2-chloro-3-[2,4-dichloro-5-(4-difluoromethyl-4,5-dihydro-3-methyl-5-oxo-1H-1,2,4-triazol-1-yl)phenyl]propionamide A stirred solution of 0.50 g (0.0013 mole) of 2-chloro-3-[2,4-dichloro-5-(4-difluoromethyl-4,5-dihydro-3-methyl-5-oxo-1H-,1,2,4-triazol-1-yl)phenyl]propionic acid (Compound A2), 0.071 g (0.0013 mole) of cyclopropylamine, 0.17 g (0.0013 mole) of 1-hydroxybenzotriazole hydrate, and 0.18 g (0.0014 mole) of N,N-diisopropylethylamine in approximately 15 mL of tetrahydrofuran was cooled to 0° C. To this cold mixture was added 0.26 g (0.0013 mole) of 1,3-dicyclohexylcarbodiimide. After complete addition, the reaction mixture was allowed to warm to room temperature and was stirred for approximately 18 hours. The reaction mixture was filtered. The filtrate was diluted with carbon tetrachloride and was washed in succession with a 1N hydrochloric acid solution, an aqueous 10% sodium hydroxide solution, water, and an aqueous saturated sodium chloride solution. The organic phase was dried over anhydrous magnesium sulfate, filtered, and the filtrate was evaporated under reduced pressure to give 0.43 g of N-cyclopropyl-2-chloro-3-[2,4-dichloro-5-(4-difluoromethyl-4,5-dihydro-3-methyl-5-oxo-1H-1,2,4-triazol-1-yl)phenyl]propionamide as a solid, m.p. 139°–143° C., Compound A17 of Table 1A.

The nmr and ir spectra were consistent with the proposed structure.

EXAMPLE 7

N-Methyl-N-methoxy-2-chloro-3-[2,4-dichloro-5-(4-difluoromethyl-4,5-dihydro-3-methyl-5-oxo-1H-1,2,4-triazol-1-yl)phenyl]propionamide A mixture of 0.50 g (0.0013 mole) of 2-chloro-3-[2,4-dichloro-5-(4-difluoromethyl-4,5-dihydro-3-methyl-5-oxo-1H-1,2,4-triazol-1-yl)phenyl]propionic acid (Compound A2) and 5 mL of thionyl chloride was stirred at reflux for three hours. The mixture was cooled, and excess thionyl chloride was removed by distillation under reduced pressure leaving a residue. The residue was added to a cold solution of 0.13 g (0.0014 mole) of N,O-dimethylhydroxylamine hydrochloride and 0.11 g (0.0014 mole) of pyridine in 20 mL of tetrahydrofuran. The resultant mixture was stirred at room temperature for approximately 18 hours. The reaction mixture was diluted with diethyl ether and was washed in succession with a 1N hydrochloric acid solution, an aqueous 10% sodium hydroxide solution, water, and an aqueous saturated sodium chloride solution. The washed organic phase was dried over anhydrous magnesium sulfate and was filtered. The filtrate was evaporated under reduced pressure to give 0.37 g of N-methyl-N-methoxy-2-chloro-3-[2,4-dichloro-5-(4-difluoromethyl-4,5-dihydro-3-methyl-5-oxo-1H-1,2,4-triazol-1-yl)phenyl]propionamide as an oil, Compound A22 of Table 1A.

The nmr and ir spectra were consistent with the proposed structure.

EXAMPLE 8

N-methylsulfonyl-2-chloro-3-[2,4-dichloro-5-(4-difluoromethyl-4,5-dihydro-3-methyl-5-oxo-1H-1,2,4-triazol-1-yl)phenyl]propionamide In a manner similar to Example 7, the reaction of 0.50 g (0.0013 mole) of 2-chloro-3-[2,4-dichloro-5-(4-difluoromethyl-4,5-dihydro-3-methyl-5-oxo-1H-1,2,4-triazol-1-yl)phenyl]propionic acid (Compound A2) with 5 mL of thionyl chloride produced a residue. To this residue was added 0.50 g (0.0052 mole) of methanesulfonamide. The mixture was stirred and heated at 120° C. for two hours. The mixture was cooled, diluted with methylene chloride, and a resultant precipitate was removed by filtration. The filtrate was washed with water. The organic phase was dried over anhydrous magnesium sulfate, filtered, and the filtrate evaporated under reduced pressure to give 0.21 g of N-methylsulfonyl-2-chloro-3-[2,4-dichloro-5-(4-difluoromethyl-4,5-dihydro-3-methyl-5-oxo-1H-1,2,4-triazol-1-yl)phenyl]propionamide as a foam, Compound A25 of Table 1A.

The nmr and ir spectra were consistent with the proposed structure.

EXAMPLE 9

2-Chloro-3-[2,4-dichloro-5-(4-difluoromethyl-4,5-dihydro-3-methyl-5-oxo-1H-1,2,4-triazol-1-yl)phenyl]-N-(4-chlorophenyl)propionamide A stirred solution of 0.50 g (0.0013 mole) of 2-chloro-3-[2,4-dichloro-5-(4-difluoromethyl-4,5-dihydro-3-methyl-5-oxo-1H-1,2,4-triazol-1-yl)phenyl]propionic acid (Compound 2), 0.16 g (0.0013 mole) of 4-chloroaniline, 0.17 g (0.0013 mole) of 1-hydroxybenzotriazole hydrate, and 0.18 g (0.0014 mole) of N,N-diisopropylethylamine in approximately 15 mL of tetrahydrofuran was cooled to 0° C. To this cold reaction mixture was added 0.26 g (0.0013 mole) of 1,3-dicyclohexylcarbodiimide. After complete addition, the reaction mixture was allowed to warm to room temperature and was stirred for approximately 18 hours. The reaction mixture was filtered. The filtrate was diluted with carbon tetrachloride and was washed in succession with a 1N hydrochloric acid solution, an aqueous 10% sodium hydroxide solution, water, and an aqueous saturated sodium chloride solution. The organic phase was dried over anhydrous magnesium sulfate, filtered, and the filtrate evaporated under reduced pressure to give 0.28 g of 2-chloro-3-[2,4-dichloro-5-(4-difluoromethyl-4,5-dihydro-3-methyl-5-oxo-1H-1,2,4-triazol-1-yl)phenyl]-N-(4-chlorophenyl)propionamide as an oil, Compound A23 of Table 1A.

The nmr and ir spectra were consistent with the proposed structure.

EXAMPLE 10

2-Chloro-3-[2-chloro-4-fluoro-5-(4-difluoromethyl-4,5-dihydro-3-methyl-5-oxo-1H-1,2,4-trizol-1-yl)phenyl]-N-(4-methylphenylsulfonyl)propionamide To a stirred solution of 0.19 g (0.0012 mole) of 1,1'-carbonyldiimidazole in 3 mL of tetrahydrofuran was added a solution of 0.45 g (0.0012 mole) of 2-chloro-3-[2-chloro-4-fluoro-5-(4-difluoromethyl-4,5-dihydro-3-methyl-5-oxo-1H-1,2,4-triazol-1-yl)phenyl]propionic acid (prepared by the method of Example 6, Step A, from 1-(5-amino-4-chloro-2-fluorophenyl)-4-difluoromethyl-4,5-dihydro-3-methyl-1,2,4-triazol-5(1H)-one) in 5 mL of tetrahydrofuran.

The reaction mixture was diluted With 5 mL of tetrahydrofuran. The mixture was stirred at room temperature for 30 minutes and then was heated at reflux for 30 minutes. The reaction mixture was cooled to room temperature, and 0.20 g (0.0012 mole) of para-toluene-sulfonamide was added. The mixture was stirred for approximately 10 minutes, and 0.17 g (0.0012 mole) of 1,8-diazabicyclo [5.4.0]undec-7-ene was added. The resultant mixture was stirred at room temperature for approximately 18 hours. The reaction mixture was partitioned between diethyl ether and 1N hydrochloric acid solution. The organic phase was washed in succession with water and an aqueous saturated sodium chloride solution. The washed organic phase was dried over anhydrous magnesium sulfate, filtered, and the filtrate evaporated under reduced pressure leaving a residue. This residue was purified by column chromatography on silica gel, eluting with n-heptane:ethanol:chloroform (1:1:1), to yield 0.23 g of 2-chloro-3-[2-chloro-4-fluoro-5-(4-difluoromethyl-4,5-dihydro-3-methyl-5-oxo-1H-1,2,4-triazol-1-yl)phenyl]-N-(4-methylphenylsulfonyl)-propionamide as a solid, m.p. 267°–269° C., Compound A38 of Table 1A.

The nmr spectrum was consistent with the proposed structure.

HERBICIDAL ACTIVITY

The plant test species used in demonstrating the herbicidal activity of compounds of this invention include cotton (*Gossypium hirsutum* var. DPL61), soybean (*Glycine max* var. Williams), field corn (*Zea mays* var. Pioneer 3732), wheat (*Triticum aestivium* var. Wheaton), rice (*Oryza sativa* var. Labelle), morningglory (*Ipomea lacumosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), and johnsongrass (*Sorghum halepense*).

Preparation of Flats

Preemergence

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below. Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to cient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |

-continued

| Herbicide Rating System | | | |
|---|---|---|---|
| Rating Percent Control | Description of Main Categories | Crop Description | Weed Description |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Tables 2, 2A, 3, and 3A below. The test compounds are identified in the tables by numbers which correspond to those in Table 1. The abbreviation "kg/ha" in Tables 2 and 3 means kilograms per hectare.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable powder formulations are:

| Component | | % by Wt. |
|---|---|---|
| Active ingredient | | 40.00 |
| Sodium lignosulfonate | | 20.00 |
| Attapulgite clay | | 40.00 |
| | Total | 100.00 |
| Active ingredient | | 90.00 |
| Dioctyl sodium sulfosuccinate | | 0.10 |
| Synthetic fine silica | | 9.90 |
| | Total | 100.00 |
| Active ingredient | | 20.00 |
| Sodium alkylnaphthalenesulfonate | | 4.00 |
| Sodium lignosulfonate | | 4.00 |
| Low viscosity methyl cellulose | | 3.00 |
| Attapulgite clay | | 69.00 |
| | Total | 100.00 |
| Active ingredient | | 25.00 |
| Base: | | 75.00 |
| 96% hydrated aluminum magnesium silicate | | |
| 2% powdered sodium lignosulfonate | | |
| 2% powdered anionic sodium alkyl-naphthalenesulfonate | | |
| | Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component | | % by Wt. |
|---|---|---|
| Active ingredient | | 53.01 |
| Blend of alkylnaphthalenesulfonate and polyoxyethylene ethers | | 6.00 |
| Epoxidized soybean oil | | 1.00 |
| Xylene | | 39.99 |
| | Total | 100.00 |
| Active ingredient | | 10.00 |
| Blend of alkylnaphthalenesulfonate and polyoxyethylene ethers | | 4.00 |
| Xylene | | 86.00 |
| | Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively nonvolatile solvent such as Water, corn oil, kerosene, propylene glycol, or other suitable solvents. The following illustrate specific suspensions:

| | % by Wt. |
|---|---|
| Oil Suspension: | |
| Active ingredient | 25.00 |
| Polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; for example, with Compound 3 (Table 1) applied postemergently, an amount in the range of about 15 to 125 g/ha, such as about 30 to 60 g/ha, may be employed for control of broad leaf weeds with tolerance for crops such as wheat and maize. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)-glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N'-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

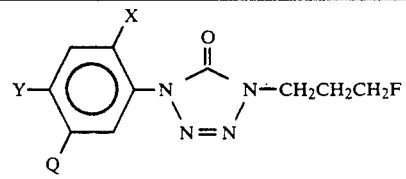

| Cmpd. No. | X | Y | Q |
|---|---|---|---|
| 1 | F | Cl | CH$_2$CH$_2$CO$_2$C$_2$H$_5$ |
| 2 | F | Cl | CH(Br)CH(Br)CO$_2$C$_2$H$_5$ |
| 3 | F | Cl | CH$_2$CH(Cl)CO$_2$C$_2$H$_5$ |
| 4 | F | Cl | CH=CHCO$_2$C$_2$H$_5$ |
| 5 | Cl | Cl | CH$_2$CH$_2$CO$_2$CH$_3$ |
| 6 | Cl | Cl | CH$_2$CH(Cl)CO$_2$H |
| 7 | Cl | Cl | CH$_2$CH(Cl)CO$_2$CH$_3$ |
| 8 | Cl | Cl | CH$_2$CH(Cl)CO$_2$C$_2$H$_5$ |
| 9 | Cl | Cl | CH$_2$CH(Br)CO$_2$C$_2$H$_5$ |
| 10 | Cl | Cl | CH$_2$CH(Cl)CO$_2$CH(CH$_3$)$_2$ |
| 11 | Cl | Cl | CH$_2$CH(Cl)CO$_2$CH(CH$_3$)CH$_2$CH$_3$ |

TABLE 1-continued

Structure: 2,4,5-trisubstituted phenyl (X at 2, Y at 4, Q at 5) attached to N of a triazolinone ring (N—CH₂CH₂CH₂F), with N=N.

| Cmpd. No. | X | Y | Q |
|---|---|---|---|
| 12 | Cl | Cl | CH₂CH(Cl)CO₂CH₂C₆H₅ |
| 13 | Cl | Cl | CH(Br)CH(Br)CO₂CH₃ |
| 14 | Cl | Cl | CH(Br)CH(Br)CO₂C₂H₅ |
| 15 | Cl | Cl | CH(CH₃)CH(Cl)CO₂C₂H₅ |
| 16 | F | Cl | CH₂C(Cl)(CH₃)CO₂CH₃ |
| 17 | Cl | Cl | CH₂CH(Cl)C(O)NH₂ |
| 18 | Cl | Cl | CH₂CH(Cl)C(O)NHCH₃ |
| 19 | Cl | Cl | CH₂CH(Cl)C(O)N(CH₃)₂ |
| 20 | Cl | Cl | CH₂CH(Cl)C(O)NH-cyclopropyl |
| 21 | Cl | Cl | CH₂CH(Cl)C(O)NHCH₂CH=CH₂ |
| 22 | Cl | Cl | CH₂CH(Cl)C(O)NHCH₂CN |
| 23 | Cl | Cl | CH₂CH(Cl)C(O)NHOH |
| 24 | Cl | Cl | CH₂CH(Cl)C(O)NHOCH₃ |
| 25 | Cl | Cl | CH₂CH(Cl)C(O)N(CH₃)OCH₃ |
| 26 | Cl | Cl | CH₂CH(Cl)C(O)NHC₆H₄-4-Cl |
| 27 | Cl | Cl | CH₂CH(Cl)C(O)NHCH₂C₆H₄-4-Cl |
| 28 | Cl | Cl | CH₂CH(Cl)C(O)NHSO₂CH₃ |
| 29 | Cl | Cl | CH₂CH(Cl)C(O)NHSO₂C₆H₄-4-Cl |
| 30 | Cl | Cl | CH₂CH(Cl)C(O)NHSO₂C₆H₄-4-CH₃ |
| 31 | F | Cl | CH₂CH(CH₃)CO₂CH₃ |
| 32 | F | Cl | CH₂CH(Cl)C(O)NH-cyclopropyl |
| 33 | F | Cl | CH₂CH(Cl)C(O)NHCH₂CN |
| 34 | F | Cl | CH₂CH(Cl)C(O)N(CH₃)OCH₃ |
| 35 | F | Cl | CH₂CH(Cl)C(O)NHSO₂CH₃ |
| 36 | F | Cl | CH₂CH(Cl)C(O)NHSO₂CF₃ |
| 37 | F | Cl | CH₂CH(Cl)C(O)NHSO₂C₆H₄-2-Cl |
| 38 | F | Cl | CH₂CH(Cl)C(O)NHSO₂C₆H₄-3-Cl |
| 39 | F | Cl | CH₂CH(Cl)C(O)NHSO₂C₆H₄-4-Cl |
| 40 | F | Cl | CH₂CH(Cl)C(O)NHSO₂CH(CH₃)₂ |
| 41 | F | Cl | CH₂CH(Cl)C(O)NHSO₂C₆H₄-4-CH₃ |
| 42 | Cl | Cl | CH=CHCO₂CH₃ |
| 43 | Cl | Cl | CH=CHCO₂C₂H₅ |
| 44 | Cl | Cl | CH=CHCO₂CH₂C₆H₅ |
| 45 | F | Cl | CH=C(CH₃)CO₂CH₃ |
| 46 | Cl | Cl | CH₂CH(Cl)CN |
| 47 | F | Cl | CH₂CH(Cl)CO₂CH₃ |
| 48 | F | Cl | CH₂CH(Cl)COOH |
| 49 | Cl | Cl | CH₂CH(Cl)COCH₃ |
| 50 | Cl | Cl | CH₂CH(Cl)CONHCH₂CH₂CH₃ |
| 51 | Cl | Cl | CH₂CH(Cl)CONHCH₂CH₂CH₃ |
| 52 | Cl | Cl | CH₂CH(Cl)CONHCH(CH₃)CH₂CH₃ |
| 53 | Cl | Cl | CH₂CH(Cl)CONH-cyclopentyl |
| 54 | Cl | Cl | CH=CHCONH-cyclopentyl |
| 55 | Cl | Cl | CH=CHCONHCH₂CH₂CH₃ |
| 56 | Cl | Cl | CH=CHCONHCH(CH₃)CH₂CH₃ |
| 57 | F | Cl | CH=CHCO₂CH₃ |
| 58 | F | Cl | CH₂CH(Cl)CO₂CH(CH₃)₂ |
| 59 | Cl | Cl | CH₂CH(Cl)CONHCH(CH₃)₂ |
| 60 | Cl | Cl | CH=CHCONHCH(CH₃)₂ |
| 61 | Cl | Cl | CH₂CH(Cl)CONHC₂H₅ |
| 62 | Cl | Cl | CH=CHCONHC₂H₅ |
| 63 | F | Cl | CH₂CH(Cl)CHO |
| 64 | F | Cl | CH₂CH(Cl)CO₂K |
| 65 | F | Cl | CH₂CH(Cl)CO₂NH(C₂H₅)₃ |
| 66 | Cl | Cl | CH₂CH(Cl)CO₂Na |
| 67 | Cl | Cl | CH₂CH(Cl)CO₂NH(C₂H₅)₃ |

TABLE 1A

Structure: 2,4,5-trisubstituted phenyl attached to N of a triazolinone ring (N—CH₂F), with =C(CH₃) substituent.

| Cmpd No. | X | Y | Q |
|---|---|---|---|
| A1 | Cl | Cl | CH₂CH₂CO₂CH₃ |

TABLE 1A-continued

| Cmpd No. | X | Y | Q |
|---|---|---|---|
| A2 | Cl | Cl | CH₂CH(Cl)CO₂H |
| A3 | Cl | Cl | CH₂CH(Cl)CO₂CH₃ |
| A4 | Cl | Cl | CH₂CH(Cl)CO₂C₂H₅ |
| A5 | F | Cl | CH₂CH(Cl)CO₂C₂H₅ |
| A6 | Cl | Cl | CH₂CH(Br)CO₂C₂H₅ |
| A7 | Cl | Cl | CH₂CH(Cl)CO₂CH(CH₃)₂ |
| A8 | Cl | Cl | CH₂CH(Cl)CO₂CH(CH₃)CH₂CH₃ |
| A9 | Cl | Cl | CH₂CH(Cl)CO₂CH₂C₆H₅ |
| A10 | Cl | Cl | CH(Br)CH(Br)CO₂CH₃ |
| A11 | Cl | Cl | CH(Br)CH(Br)CO₂C₂H₅ |
| A12 | Cl | Cl | CH(CH₃)CH(Cl)CO₂C₂H₅ |
| A13 | F | Cl | CH₂C(Cl)(CH₃)CO₂CH₃ |
| A14 | Cl | Cl | CH₂CH(Cl)C(O)NH₂ |
| A15 | Cl | Cl | CH₂CH(Cl)C(O)NHCH₃ |
| A16 | Cl | Cl | CH₂CH(Cl)C(O)N(CH₃)₂ |
| A17 | Cl | Cl | CH₂CH(Cl)C(O)NH-cyclopropyl |
| A18 | Cl | Cl | CH₂CH(Cl)C(O)NHCH₂CH=CH₂ |
| A19 | Cl | Cl | CH₂CH(Cl)C(O)NHCH₂CN |
| A20 | Cl | Cl | CH₂CH(Cl)C(O)NHOH |
| A21 | Cl | Cl | CH₂CH(Cl)C(O)NHOCH₃ |
| A22 | Cl | Cl | CH₂CH(Cl)C(O)N(CH₃)OCH₃ |
| A23 | Cl | Cl | CH₂CH(Cl)C(O)NHC₆H₄-4-Cl |
| A24 | Cl | Cl | CH₂CH(Cl)C(O)NHCH₂C₆H₄-4-Cl |
| A25 | Cl | Cl | CH₂CH(Cl)C(O)NHSO₂CH₃ |
| A26 | Cl | Cl | CH₂CH(Cl)C(O)NHSO₂C₆H₄-4-Cl |
| A27 | Cl | Cl | CH₂CH(Cl)C(O)NHSO₂C₆H₄-4-CH₃ |
| A28 | F | Cl | CH₂CH(CH₃)CO₂CH₃ |
| A29 | F | Cl | CH₂CH(Cl)C(O)NH-cyclopropyl |
| A30 | F | Cl | CH₂CH(Cl)C(O)NHCH₂CN |
| A31 | F | Cl | CH₂CH(Cl)C(O)N(CH₃)OCH₃ |
| A32 | F | Cl | CH₂CH(Cl)C(O)NHSO₂CH₃ |
| A33 | F | Cl | CH₂CH(Cl)C(O)NHSO₂CF₃ |
| A34 | F | Cl | CH₂CH(Cl)C(O)NHSO₂C₆H₄-2-Cl |
| A35 | F | Cl | CH₂CH(Cl)C(O)NHSO₂C₆H₄-3-Cl |
| A36 | F | Cl | CH₂CH(Cl)C(O)NHSO₂C₆H₄-4-Cl |
| A37 | F | Cl | CH₂CH(Cl)C(O)NHSO₂CH(CH₃)₂ |
| A38 | F | Cl | CH₂CH(Cl)C(O)NHSO₂C₆H₄-4-CH₃ |
| A39 | Cl | Cl | CH=CHCO₂CH₃ |
| A40 | Cl | Cl | CH=CHCO₂C₂H₅ |
| A41 | F | Cl | CH=CHCO₂C₂H₅ |
| A42 | Cl | Cl | CH=CHCO₂CH₂C₆H₅ |
| A43 | F | Cl | CH=C(CH₃)CO₂CH₃ |
| A44 | Cl | Cl | CH₂CH(Cl)CN |
| A45 | F | Cl | CH₂CH(Cl)CO₂CH₃ |
| A46 | F | Cl | CH₂CH(Cl)COOH |
| A47 | Cl | Cl | CH₂CH(Cl)COCH₃ |
| A48 | Cl | Cl | CH₂CH(Cl)CONHCH₂CH₂CH₃ |
| A49 | Cl | Cl | CH₂CH(Cl)CONHCH₂CH₂CH₃ |
| A50 | Cl | Cl | CH₂CH(Cl)CONHCH(CH₃)CH₂CH₃ |
| A51 | Cl | Cl | CH₂CH(Cl)CONH-cyclopentyl |
| A52 | Cl | Cl | CH=CHCONH-cyclopentyl |
| A53 | Cl | Cl | CH=CHCONHCH₂CH₂CH₃ |
| A54 | Cl | Cl | CH=CHCONHCH(CH₃)CH₂CH₃ |
| A55 | F | Cl | CH=CHCO₂CH₃ |
| A56 | F | Cl | CH₂CH(Cl)CO₂CH(CH₃)₂ |
| A57 | Cl | Cl | CH₂CH(Cl)CONHCH(CH₃)₂ |
| A58 | Cl | Cl | CH=CHCONHCH(CH₃)₂ |
| A59 | Cl | Cl | CH₂CH(Cl)CONHC₂H₅ |
| A60 | Cl | Cl | CH=CHCONHC₂H₅ |
| A61 | F | Cl | CH₂CH(Cl)CHO |

TABLE 1B where NHet is a 6-membered ring: —N attached to ring with C=O, N—CH₃, C=O, N, CH=CH (triazinedione structure)

| Cmpd No. | X | Y | Q |
|---|---|---|---|
| B1 | F | Cl | $CH_2CH_2CO_2C_2H_5$ |
| B2 | F | Cl | $CH(Br)CH(Br)CO_2C_2H_5$ |
| B3 | F | Cl | $CH_2CH(Cl)CO_2C_2H_5$ |
| B4 | F | Cl | $CH=CHCO_2C_2H_5$ |
| B5 | Cl | Cl | $CH_2CH_2CO_2CH_3$ |
| B6 | Cl | Cl | $CH_2CH(Cl)CO_2H$ |
| B7 | Cl | Cl | $CH_2CH(Cl)CO_2CH_3$ |
| B8 | Cl | Cl | $CH_2CH(Cl)CO_2C_2H_5$ |
| B9 | Cl | Cl | $CH_2CH(Br)CO_2C_2H_5$ |
| B10 | Cl | Cl | $CH_2CH(Cl)CO_2CH(CH_3)_2$ |
| B11 | Cl | Cl | $CH_2CH(Cl)CO_2CH(CH_3)CH_2CH_3$ |
| B12 | Cl | Cl | $CH_2CH(Cl)CO_2CH_2C_6H_5$ |
| B13 | Cl | Cl | $CH(Br)CH(Br)CO_2CH_3$ |
| B14 | Cl | Cl | $CH(Br)CH(Br)CO_2C_2H_5$ |
| B15 | Cl | Cl | $CH(CH_3)CH(Cl)CO_2C_2H_5$ |
| B16 | F | Cl | $CH_2C(Cl)(CH_3)CO_2CH_3$ |
| B17 | Cl | Cl | $CH_2CH(Cl)C(O)NH_2$ |
| B18 | Cl | Cl | $CH_2CH(Cl)C(O)NHCH_3$ |
| B19 | Cl | Cl | $CH_2CH(Cl)C(O)N(CH_3)_2$ |
| B20 | Cl | Cl | $CH_2CH(Cl)C(O)NH$-cyclopropyl |
| B21 | Cl | Cl | $CH_2CH(Cl)C(O)NHCH_2CH=CH_2$ |
| B22 | Cl | Cl | $CH_2CH(Cl)C(O)NHCH_2CN$ |
| B23 | Cl | Cl | $CH_2CH(Cl)C(O)NHOH$ |
| B24 | Cl | Cl | $CH_2CH(Cl)C(O)NHOCH_3$ |
| B25 | Cl | Cl | $CH_2CH(Cl)C(O)N(CH_3)OCH_3$ |
| B26 | Cl | Cl | $CH_2CH(Cl)C(O)NHC_6H_4$-4-Cl |
| B27 | Cl | Cl | $CH_2CH(Cl)C(O)NHCH_2C_6H_4$-4-Cl |
| B28 | Cl | Cl | $CH_2CH(Cl)C(O)NHSO_2CH_3$ |
| B29 | Cl | Cl | $CH_2CH(Cl)C(O)NHSO_2C_6H_4$-4-Cl |
| B30 | Cl | Cl | $CH_2CH(Cl)C(O)NHSO_2C_6H_4$-4-$CH_3$ |
| B31 | F | Cl | $CH_2CH(CH_3)CO_2CH_3$ |
| B32 | F | Cl | $CH_2CH(Cl)C(O)NH$-cyclopropyl |
| B33 | F | Cl | $CH_2CH(Cl)C(O)NHCH_2CN$ |
| B34 | F | Cl | $CH_2CH(Cl)C(O)N(CH_3)OCH_3$ |
| B35 | F | Cl | $CH_2CH(Cl)C(O)NHSO_2CH_3$ |
| B36 | F | Cl | $CH_2CH(Cl)C(O)NHSO_2CF_3$ |
| B37 | F | Cl | $CH_2CH(Cl)C(O)NHSO_2C_6H_4$-2-Cl |
| B38 | F | Cl | $CH_2CH(Cl)C(O)NHSO_2C_6H_4$-3-Cl |
| B39 | F | Cl | $CH_2CH(Cl)C(O)NHSO_2C_6H_4$-4-Cl |
| B40 | F | Cl | $CH_2CH(Cl)C(O)NHSO_2CH(CH_3)_2$ |
| B41 | F | Cl | $CH_2CH(Cl)C(O)NHSO_2C_6H_4$-4-$CH_3$ |
| B42 | Cl | Cl | $CH=CHCO_2CH_3$ |
| B43 | Cl | Cl | $CH=CHCO_2C_2H_5$ |
| B44 | Cl | Cl | $CH=CHCO_2CH_2C_6H_5$ |
| B45 | F | Cl | $CH=C(CH_3)CO_2CH_3$ |
| B46 | Cl | Cl | $CH_2CH(Cl)CN$ |
| B47 | F | Cl | $CH_2CH(Cl)CO_2CH_3$ |
| B48 | F | Cl | $CH_2CH(Cl)COOH$ |
| B49 | Cl | Cl | $CH_2CH(Cl)COCH_3$ |
| B50 | Cl | Cl | $CH_2CH(Cl)CONHCH_2CH_2CH_3$ |
| B51 | Cl | Cl | $CH_2CH(Cl)CONHCH_2CH_2CH_2CH_3$ |
| B52 | Cl | Cl | $CH_2CH(Cl)CONHCH(CH_3)CH_2CH_3$ |
| B53 | Cl | Cl | $CH_2CH(Cl)CONH$-cyclopentyl |
| B54 | Cl | Cl | $CH=CHCONH$-cyclopentyl |
| B55 | Cl | Cl | $CH=CHCONHCH_2CH_2CH_2CH_3$ |
| B56 | Cl | Cl | $CH=CHCONHCH(CH_3)CH_2CH_3$ |
| B57 | F | Cl | $CH=CHCO_2CH_3$ |
| B58 | F | Cl | $CH_2CH(Cl)CO_2CH(CH(CH_3)_2)$ |
| B59 | Cl | Cl | $CH_2CH(Cl)CONHCH(CH_3)_2$ |
| B60 | Cl | Cl | $CH=CHCONHCH(CH_3)_2$ |
| B61 | Cl | Cl | $CH_2CH(Cl)CONHC_2H_5$ |
| B62 | Cl | Cl | $CH=CHCONHC_2H_5$ |
| B63 | F | Cl | $CH_2CH(Cl)CHO$ |
| B64 | F | Cl | $CH_2CH(Cl)CO_2K$ |
| B65 | F | Cl | $CH_2CH(Cl)CO_2NH(C_2H_5)_3$ |
| B66 | Cl | Cl | $CH_2CH(Cl)CO_2Na$ |
| B67 | Cl | Cl | $CH_2CH(Cl)CO_2NH(C_2H_5)_2$ |

Other representative compounds are compounds C1 to C67 which are identical with each of compounds B1 to B67 above except that in each case NHet is 3-chloro-4,5,6,7-tetrahydro-2H-indazol-2-yl (chloro-substituted tetrahydroindazole attached via N)

Other representative compounds are compounds D1 to D67 which are identical with each of compounds B1 to B67 above except that in each case NHet is hexahydropyridazine-1,2-dicarbonyl bicyclic diketone (N–N bicyclic with two C=O groups)

Other representative compounds are compounds E1 to E67 which are identical with each of compounds B1 to B67 above except that in each case NHet is hexahydroimidazo[1,2-a]pyridine-1,3-dione (bicyclic N–N with two C=O groups)

Other representative compounds are compounds F1 to F67 which are identical with each of compounds B1 to B67 above except that in each case NHet is —N—C(O)—N(CH₃)—CH(H)—C(O)—NH— (6-membered ring with two N, NH, and C=O groups)

Other representative compounds are compounds G1 to G67 which are identical with each of compounds B1 to B67 above except that in each case NHet is

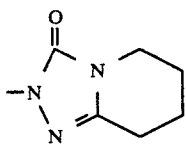

Other representative compounds are compounds H1 to H67 which are identical with each of compounds B1 to B67 above except that in each case NHet is

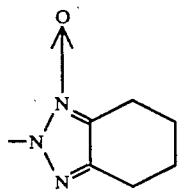

Other representative compounds are compounds I1 to I67 which are identical with each of compounds B1 to B67 above except that in each case NHet is

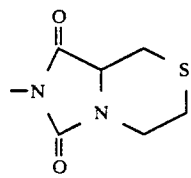

Other representative compounds are compounds J1 to J67 which are identical with each of compounds B1 to B67 above except that in each case NHet is

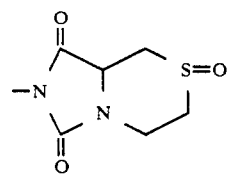

Other representative compounds are compounds K1 to K67 which are identical with each of compounds B1 to B67 above except that in each case NHet is

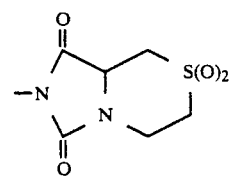

Other representative compounds are compounds M1 to M67 which are identical with each of compounds B1 to B67 above except that in each case NHet is

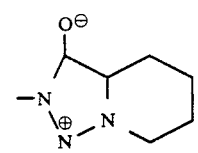

Other representative compounds are compounds N1 to N67 which are identical with each of compounds B1 to B67 above except that in each case NHet is

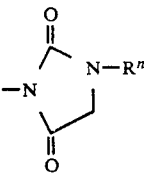

where $R^n$ is isopropyl.

Other representative compounds are identical to compounds N1 to N67 except that $R^n$ is $CH_3$. Other representative compounds are those which are identical to N1 to N67 except that $R^n$ is $C_2H_5$. Still other representative compounds are identical to N1 to N67 except that $R^n$ is $CH_2CH_2CH_3$. Other representative compounds are identical to N1 to N67 except that $R^n$ is $CH_2CH_2CH_2F$.

Other representative compounds are compounds P1 to P67 which are identical with each of compounds B1 to B67 above except that in each case NHet is

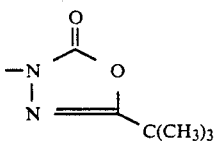

Other representative compounds are compounds Q1 to Q67 which are identical with each of compounds B1 to B67 above except that in each case NHet is

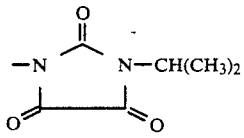

Other representative compounds are compounds R1 to R67 which are identical with each of compounds B1 to B67 above except that in each case NHet is

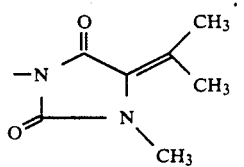

Other representative compounds are compounds S1 to S67 which are identical with each of compounds B1 to B67 above except that in each case NHet is

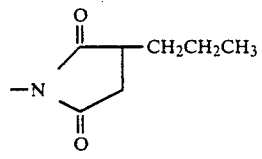
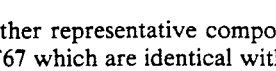

Other representative compounds are compounds T1 to T67 which are identical with each of compounds B1 to B67 above except that in each case NHet is

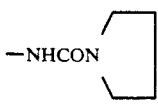

Other representative compounds are compounds U1 to U67 which are identical with each of compounds B1 to B67 above except that in each case NHet is

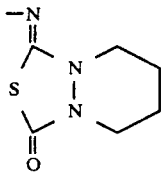

Other representative compounds are compounds V1 to V67 which are identical with each of compounds B1 to B67 above except that in each case NHet is

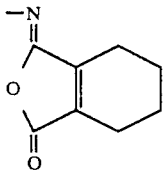

Other representative compounds are compounds W1 to W67 which are identical with each of compounds B1 to B67 above except that in each case NHet is

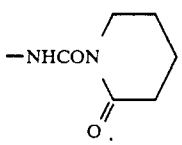

Other representative compounds are compounds X1 to X67 which are identical with each of compounds B1 to B67 above except that in each case NHet is

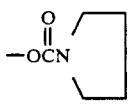

Other representative compounds are compounds XA1-XA67 which are identical to each of compounds B1 to B67 above except that in each case NHet is

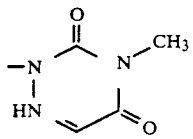

TABLE 2

| Cmpd. No. Species | Preemergence Herbicidal Activity % Control @ 0.5 kg/ha | | | |
|---|---|---|---|---|
| | 1 | 2 | 3 | 4 |
| Cotton | 30 | 20 | 95 | 40 |

TABLE 2-continued

| Cmpd. No. Species | Preemergence Herbicidal Activity % Control @ 0.5 kg/ha | | | |
|---|---|---|---|---|
| | 1 | 2 | 3 | 4 |
| Soybean | 5 | 5 | 0 | 10 |
| Corn | 5 | 10 | 5 | 5 |
| Rice | 30 | 5 | 20 | 20 |
| Wheat | 5 | 5 | 15 | 30 |
| Morningglory | 10 | 80 | 100 | 80 |
| Wild Mustard | 100 | 100 | 100 | 100 |
| Velvetleaf | 100 | 100 | 100 | 100 |
| Barnyardgrass | 80 | 40 | 20 | 80 |
| Green Foxtail | 70 | 0 | 60 | 70 |
| Johnsongrass | 90 | 5 | 70 | 70 |

TABLE 2A

PREEMERGENCE HERBICIDAL ACTIVITY (% CONTROL)

| | Compound No. | | |
|---|---|---|---|
| | 1A | 2A | 3A |
| | Rate (kg/ha) | | |
| Species | 0.5 | 0.5 | 0.5 |
| Cotton | 0 | 90 | 50 |
| Soybean | 0 | 0 | 5 |
| Field Corn | 30 | 10 | 10 |
| Rice | 60 | 10 | 5 |
| Wheat | 5 | 0 | 5 |
| Morningglory | 50 | 100 | 95 |
| Wild Mustard | 70 | 90 | 100 |
| Velvetleaf | 95 | 100 | 100 |
| Barnyardgrass | 30 | 5 | 70 |
| Green Foxtail | 50 | 10 | 85 |
| Johnsongrass | 50 | 30 | 50 |

| | Compound No. | | |
|---|---|---|---|
| | 4A | 5A | 6A |
| | Rate (kg/ha) | | |
| Species | 0.5 | 0.5 | 0.5 |
| Cotton | 70 | 90 | 30 |
| Soybean | 5 | 0 | 5 |
| Field Corn | 10 | 5 | 10 |
| Rice | 15 | 10 | 5 |
| Wheat | 10 | 20 | 0 |
| Morningglory | 100 | 100 | 50 |
| Wild Mustard | 100 | 100 | 60 |
| Velvetleaf | 100 | 100 | 100 |
| Barnyardgrass | 40 | 20 | 0 |
| Green Foxtail | 5 | 5 | 0 |
| Johnsongrass | 70 | 40 | 5 |

| | Compound No. | | |
|---|---|---|---|
| | 7A | 8A | 9A |
| | Rate (kg/ha) | | |
| Species | 0.5 | 0.5 | 0.5 |
| Cotton | 90 | 80 | 80 |
| Soybean | 0 | 0 | 0 |
| Field Corn | 15 | 10 | 10 |
| Rice | 15 | 5 | 30 |
| Wheat | 0 | 0 | 5 |
| Morningglory | 90 | 40 | 100 |
| Wild Mustard | 100 | 90 | 95 |
| Velvetleaf | 95 | 100 | 100 |
| Barnyardgrass | 50 | 5 | 70 |
| Green Foxtail | 50 | 10 | 30 |
| Johnsongrass | 20 | 60 | 85 |

| | Compound No. | | |
|---|---|---|---|
| | 10A | 11A | 12A |
| | Rate (kg/ha) | | |
| Species | 0.5 | 0.5 | 0.5 |
| Cotton | 5 | 10 | 50 |
| Soybean | 10 | 0 | 0 |
| Field Corn | 0 | 20 | 40 |
| Rice | 15 | 40 | 30 |
| Wheat | 0 | 5 | 60 |
| Morningglory | 30 | 50 | 100 |

TABLE 2A-continued
PREEMERGENCE HERBICIDAL ACTIVITY
(% CONTROL)

| | | | |
|---|---|---|---|
| Wild Mustard | 100 | 100 | 95 |
| Velvetleaf | 100 | 100 | 100 |
| Barnyardgrass | 85 | 100 | 95 |
| Green Foxtail | 100 | 95 | 100 |
| Johnsongrass | 50 | 90 | 85 |

| | Compound No. | | |
|---|---|---|---|
| | 13A | 14A | 15A |
| | Rate (kg/ha) | | |
| Species | 0.5 | 0.5 | 0.5 |
| Cotton | 30 | 90 | 80 |
| Soybean | 0 | 95 | 95 |
| Field Corn | 10 | 95 | 95 |
| Rice | 5 | 95 | 95 |
| Wheat | 20 | 95 | 95 |
| Morningglory | 100 | 100 | 95 |
| Wild Mustard | 100 | 100 | 100 |
| Velvetleaf | 100 | 100 | 100 |
| Barnyardgrass | 60 | 100 | 95 |
| Green Foxtail | 5 | 100 | 100 |
| Johnsongrass | 30 | 100 | 100 |

| | Compound No. | | |
|---|---|---|---|
| | 16A | 17A | 18A |
| | Rate (kg/ha) | | |
| Species | 0.5 | 0.5 | 0.5 |
| Cotton | 80 | 60 | 70 |
| Soybean | 90 | 100 | 90 |
| Field Corn | 95 | 95 | 90 |
| Rice | 95 | 90 | 90 |
| Wheat | 95 | 100 | 95 |
| Morningglory | 70 | 100 | 95 |
| Wild Mustard | 100 | 100 | 100 |
| Velvetleaf | 100 | 100 | 100 |
| Barnyardgrass | 95 | 100 | 90 |
| Green Foxtail | 100 | 100 | 100 |
| Johnsongrass | 95 | 100 | 95 |

| | Compound No. | | |
|---|---|---|---|
| | 19A | 22A | 23A |
| | Rate (kg/ha) | | |
| Species | 0.5 | 0.5 | 0.5 |
| Cotton | 20 | 40 | 15 |
| Soybean | 50 | 5 | 5 |
| Field Corn | 80 | 85 | 0 |
| Rice | 60 | 30 | 5 |
| Wheat | 95 | 90 | 0 |
| Morningglory | 100 | 95 | 15 |
| Wild Mustard | 100 | 100 | 95 |
| Velvetleaf | 100 | 100 | 100 |
| Barnyardgrass | 95 | 100 | 5 |
| Green Foxtail | 95 | 100 | 95 |
| Johnsongrass | 100 | 95 | 20 |

| | Compound No. | | |
|---|---|---|---|
| | 24A | 25A | 26A |
| | Rate (kg/ha) | | |
| Species | 0.5 | 0.5 | 0.5 |
| Cotton | 30 | 80 | 85 |
| Soybean | 10 | 5 | 5 |
| Field Corn | 5 | 80 | 50 |
| Rice | 5 | 40 | 40 |
| Wheat | 5 | 85 | 50 |
| Morningglory | 50 | 100 | 80 |
| Wild Mustard | 100 | 100 | 100 |
| Velvetleaf | 100 | 100 | 100 |
| Barnyardgrass | 70 | 70 | 15 |
| Green Foxtail | 100 | 95 | 60 |
| Johnsongrass | 50 | 80 | 50 |

| | Compound No. | | |
|---|---|---|---|
| | 27A | 28A | 29A |
| | Rate (kg/ha) | | |
| Species | 0.5 | 0.25 | 0.5 |
| Cotton | 10 | 0 | 100 |
| Soybean | 5 | 0 | 100 |
| Field Corn | 70 | 5 | 100 |
| Rice | 40 | 5 | 100 |
| Wheat | 70 | 15 | 100 |
| Morningglory | 85 | 20 | 100 |
| Wild Mustard | 100 | 50 | 100 |
| Velvetleaf | 100 | 100 | 100 |
| Barnyardgrass | 80 | 40 | 100 |
| Green Foxtail | 95 | 0 | 100 |
| Johnsongrass | 70 | 20 | 100 |

| | Compound No. | | |
|---|---|---|---|
| | 30A | 31A | 33A |
| | Rate (kg/ha) | | |
| Species | 0.25 | 0.5 | 0.25 |
| Cotton | 80 | 70 | 10 |
| Soybean | 80 | 100 | 0 |
| Field Corn | 85 | 95 | 15 |
| Rice | 95 | 85 | 0 |
| Wheat | 95 | 95 | 5 |
| Morningglory | 100 | 100 | 85 |
| Wild Mustard | 100 | 100 | 90 |
| Velvetleaf | 100 | 100 | 95 |
| Barnyardgrass | 80 | 100 | 5 |
| Green Foxtail | 100 | 100 | 5 |
| Johnsongrass | 85 | 95 | 15 |

| | Compound No. | | |
|---|---|---|---|
| | 34A | 36A | 37A |
| | Rate (kg/ha) | | |
| Species | 0.25 | 0.25 | 0.25 |
| Cotton | 95 | 30 | 70 |
| Soybean | 0 | 0 | 5 |
| Field Corn | 5 | 15 | 30 |
| Rice | 5 | 5 | 40 |
| Wheat | 5 | 10 | 15 |
| Morningglory | 100 | 100 | 100 |
| Wild Mustard | 95 | 100 | 100 |
| Velvetleaf | 100 | 100 | 100 |
| Barnyardgrass | 5 | 90 | 30 |
| Green Foxtail | 0 | 85 | 0 |
| Johnsongrass | 10 | 10 | 30 |

| | Compound No. | | |
|---|---|---|---|
| | 39A | 40A | 41A |
| | Rate (kg/ha) | | |
| Species | 0.5 | 0.5 | 0.5 |
| Cotton | 30 | 10 | 20 |
| Soybean | 10 | 15 | 0 |
| Field Corn | 30 | 30 | 10 |
| Rice | 60 | 40 | 10 |
| Wheat | 10 | 5 | 30 |
| Morningglory | 5 | 20 | 95 |
| Wild Mustard | 95 | 100 | 100 |
| Velvetleaf | 95 | 100 | 100 |
| Barnyardgrass | 80 | 90 | 10 |
| Green Foxtail | 100 | 100 | 70 |
| Johnsongrass | 95 | 30 | 20 |

| | Compound No. | |
|---|---|---|
| | 42A | 43A |
| | Rate (kg/ha) | |
| Species | 0.5 | 0.5 |
| Cotton | 90 | 5 |
| Soybean | 5 | 5 |
| Field Corn | 5 | 10 |
| Rice | 15 | 10 |
| Wheat | 5 | 10 |
| Morningglory | 20 | 80 |
| Wild Mustard | 80 | 100 |
| Velvetleaf | 10 | 100 |
| Barnyardgrass | 20 | 50 |
| Green Foxtail | 50 | 100 |
| Johnsongrass | 20 | 40 |

TABLE 3

Postemergence Herbicidal Activity
% Control @ 0.5 kg/ha

| Cmpd. No. Species | 1 | 2 | 3 | 4 |
|---|---|---|---|---|
| Species Cotton | 100 | 90 | 100 | 100 |
| Soybean | 70 | 60 | 90 | 75 |
| Corn | 60 | 50 | 30 | 70 |
| Rice | 40 | 15 | 50 | 30 |
| Wheat | 30 | 40 | 95 | 70 |
| Morningglory | 85 | 95 | 100 | 90 |
| Wild Mustard | 100 | 100 | 100 | 100 |
| Velvetleaf | 100 | 100 | 100 | 100 |
| Barnyardgrass | 50 | 10 | 15 | 50 |
| Green Foxtail | 60 | 30 | 15 | 90 |
| Johnsongrass | 90 | — | 95 | 80 |

TABLE A

POSTEMERGENCE HERBICIDAL ACTIVITY (% CONTROL)

| | Compound No. | | |
|---|---|---|---|
| | 1A | 2A | 3A |
| | Rate (kg/ha) | | |
| Species | 0.5 | 0.5 | 0.5 |
| Cotton | 95 | 100 | 100 |
| Soybean | 50 | 40 | 60 |
| Field Corn | 50 | 30 | 60 |
| Rice | 20 | 30 | 40 |
| Wheat | 30 | 40 | 20 |
| Morningglory | 90 | 95 | 100 |
| Wild Mustard | 80 | 95 | 100 |
| Velvetleaf | 100 | 100 | 100 |
| Barnyardgrass | 50 | 30 | 70 |
| Green Foxtail | 50 | 15 | 95 |
| Johnsongrass | 30 | ND | 80 |

| | Compound No. | | |
|---|---|---|---|
| | 4A | 5A | 6A |
| | Rate (kg/ha) | | |
| Species | 0.5 | 0.5 | 0.5 |
| Cotton | 90 | 100 | 100 |
| Soybean | 80 | 80 | 40 |
| Field Corn | 50 | 50 | 40 |
| Rice | 50 | 60 | 15 |
| Wheat | 50 | 80 | 30 |
| Morningglory | 100 | 100 | 90 |
| Wild Mustard | 100 | 100 | 95 |
| Velvetleaf | 100 | 100 | 100 |
| Barnyardgrass | 85 | 90 | 20 |
| Green Foxtail | 50 | 100 | 15 |
| Johnsongrass | ND | 70 | 10 |

| | Compound No. | | |
|---|---|---|---|
| | 7A | 8A | 9A |
| | Rate (kg/ha) | | |
| Species | 0.5 | 0.5 | 0.5 |
| Cotton | 100 | 100 | 100 |
| Soybean | 80 | 50 | 95 |
| Field Corn | 40 | 40 | 50 |
| Rice | 40 | 20 | 20 |
| Wheat | 40 | 40 | 20 |
| Morningglory | 100 | 100 | 100 |
| Wild Mustard | 100 | 100 | 100 |
| Velvetleaf | 100 | 100 | 100 |
| Barnyardgrass | 60 | 40 | 20 |
| Green Foxtail | 30 | 40 | 15 |
| Johnsongrass | 40 | 30 | 40 |

| | Compound No. | | |
|---|---|---|---|
| | 10A | 11A | 12A |
| | Rate (kg/ha) | | |
| Species | 0.5 | 0.5 | 0.5 |
| Cotton | 100 | 95 | 100 |
| Soybean | 60 | 40 | 60 |
| Field Corn | 50 | 50 | 70 |
| Rice | 20 | 15 | 50 |
| Wheat | 40 | 30 | 95 |

TABLE A-continued

POSTEMERGENCE HERBICIDAL ACTIVITY (% CONTROL)

| Morningglory | 90 | 90 | 100 |
|---|---|---|---|
| Wild Mustard | 95 | 70 | 95 |
| Velvetleaf | 100 | 100 | 100 |
| Barnyardgrass | 70 | 90 | 95 |
| Green Foxtail | 40 | 50 | 85 |
| Johnsongrass | ND | ND | 95 |

| | Compound No. | | |
|---|---|---|---|
| | 13A | 14A | 15A |
| | Rate (kg/ha) | | |
| Species | 0.5 | 0.5 | 0.5 |
| Cotton | 100 | 100 | 100 |
| Soybean | 70 | 85 | 95 |
| Field Corn | 50 | 70 | 90 |
| Rice | 50 | 30 | 90 |
| Wheat | 90 | 90 | 90 |
| Morningglory | 100 | 100 | 100 |
| Wild Mustard | 100 | 100 | 95 |
| Velvetleaf | 100 | 100 | 100 |
| Barnyardgrass | 95 | 95 | 100 |
| Green Foxtail | 100 | 95 | 100 |
| Johnsongrass | 70 | ND | 90 |

| | Compound No. | | |
|---|---|---|---|
| | 16A | 17A | 18A |
| | Rate (kg/ha) | | |
| Species | 0.5 | 0.5 | 0.5 |
| Cotton | 95 | 100 | 100 |
| Soybean | 80 | 100 | 80 |
| Field Corn | 80 | 100 | 70 |
| Rice | 70 | 95 | 80 |
| Wheat | 80 | 100 | 90 |
| Morningglory | 100 | 100 | 95 |
| Wild Mustard | 85 | 100 | 85 |
| Velvetleaf | 100 | 100 | 100 |
| Barnyardgrass | 100 | 95 | 70 |
| Green Foxtail | 95 | 100 | 100 |
| Johnsongrass | 85 | 95 | 80 |

| | Compound No. | | |
|---|---|---|---|
| | 19A | 22A | 23A |
| | Rate (kg/ha) | | |
| Species | 0.5 | 0.5 | 0.5 |
| Cotton | 100 | 100 | 70 |
| Soybean | 90 | 50 | 40 |
| Field Corn | 95 | 85 | 60 |
| Rice | 80 | 40 | 25 |
| Wheat | 100 | 80 | 30 |
| Morningglory | 100 | 100 | 90 |
| Wild Mustard | 80 | 80 | 80 |
| Velvetleaf | 100 | 100 | 90 |
| Barnyardgrass | 60 | 85 | 20 |
| Green Foxtail | 90 | 90 | 40 |
| Johnsongrass | 95 | 95 | 40 |

| | Compound No. | | |
|---|---|---|---|
| | 24A | 25A | 26A |
| | Rate (kg/ha) | | |
| Species | 0.5 | 0.5 | 0.5 |
| Cotton | 100 | 100 | 100 |
| Soybean | 80 | 70 | 90 |
| Field Corn | 60 | 85 | 60 |
| Rice | 10 | 60 | 40 |
| Wheat | 20 | 60 | 40 |
| Morningglory | 100 | 100 | 100 |
| Wild Mustard | 80 | 100 | 95 |
| Velvetleaf | 100 | 100 | 100 |
| Barnyardgrass | 40 | 30 | 70 |
| Green Foxtail | 80 | 70 | 95 |
| Johnsongrass | 60 | 100 | 60 |

| | Compound No. | | |
|---|---|---|---|
| | 27A | 28A | 29A |
| | Rate (kg/ha) | | |
| Species | 0.5 | 0.25 | 0.5 |
| Cotton | 100 | 80 | 100 |
| Soybean | 80 | 60 | 95 |

TABLE A-continued

POSTEMERGENCE HERBICIDAL ACTIVITY (% CONTROL)

| Species | | | |
|---|---|---|---|
| Field Corn | 85 | 80 | 100 |
| Rice | 60 | 50 | 95 |
| Wheat | 80 | 60 | 100 |
| Morningglory | 100 | 85 | 100 |
| Wild Mustard | 100 | 90 | 100 |
| Velvetleaf | 100 | 100 | 100 |
| Barnyardgrass | 30 | 30 | 100 |
| Green Foxtail | 60 | 95 | 100 |
| Johnsongrass | 80 | 60 | 100 |

| | Compound No. | | |
|---|---|---|---|
| | 30A | 31A | 33A |
| | Rate (kg/ha) | | |
| Species | 0.25 | 0.5 | 0.25 |
| Cotton | 100 | 100 | 100 |
| Soybean | 85 | 85 | 80 |
| Field Corn | 80 | 70 | 50 |
| Rice | 70 | 60 | 15 |
| Wheat | 100 | 100 | 20 |
| Morningglory | 100 | 100 | 100 |
| Wild Mustard | 100 | 100 | 100 |
| Velvetleaf | 100 | 100 | 100 |
| Barnyardgrass | 50 | 95 | 30 |
| Green Foxtail | 100 | 95 | 15 |
| Johnsongrass | 95 | 95 | 20 |

| | Compound No. | | |
|---|---|---|---|
| | 34A | 36A | 37A |
| | Rate (kg/ha) | | |
| Species | 0.25 | 0.25 | 0.25 |
| Cotton | 100 | 100 | 100 |
| Soybean | 60 | 40 | 70 |
| Field Corn | 30 | 60 | 70 |
| Rice | 20 | 10 | 40 |
| Wheat | 50 | 20 | 20 |
| Morningglory | 100 | 100 | 100 |
| Wild Mustard | 100 | 100 | 100 |
| Velvetleaf | 100 | 100 | 100 |
| Barnyardgrass | 60 | 90 | 50 |
| Green Foxtail | 70 | 100 | 5 |
| Johnsongrass | 50 | 30 | 30 |

| | Compound No. | | |
|---|---|---|---|
| | 39A | 30A | 41A |
| | Rate (kg/ha) | | |
| Species | 0.5 | 0.5 | 0.5 |
| Cotton | 70 | 90 | 100 |
| Soybean | 40 | 40 | 95 |
| Field Corn | 70 | 50 | 70 |
| Rice | 40 | 15 | 70 |
| Wheat | 30 | 40 | 70 |
| Morningglory | 70 | 90 | 100 |
| Wild Mustard | 100 | 80 | 100 |
| Velvetleaf | 100 | 95 | 100 |
| Barnyardgrass | 70 | 80 | 95 |
| Green Foxtail | 80 | 40 | 100 |
| Johnsongrass | 85 | ND | 80 |

| | Compound No. | |
|---|---|---|
| | 42A | 43A |
| | Rate (kg/ha) | |
| Species | 0.5 | 0.5 |
| Cotton | 100 | 100 |
| Soybean | 40 | 100 |
| Field Corn | 70 | 100 |
| Rice | 15 | 60 |
| Wheat | 15 | 95 |
| Morningglory | 100 | 100 |
| Wild Mustard | 90 | 100 |
| Velvetleaf | 100 | 100 |
| Barnyardgrass | 5 | 95 |
| Green Foxtail | 10 | 100 |
| Johnsongrass | 60 | 70 |

I claim:

1. A herbicidal compound of the formula

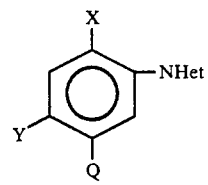

in which Q is $-CR^1(R^2)C(R^3)(R^4)Q'$ or $-CR^1=C(R^4)Q'$;

$R^1$, $R^2$ and $R^3$ are each, independently, hydrogen, halogen, or lower alkyl;

$R^4$ is hydrogen or lower alkyl;

Q' is $-COOH$, $-COOZ$, $-COOR^5$, $-CON(R^6)(R^7)$, $-CHO$ or $-C(O)R^5$;

Z is a salt-forming cation;

$R^5$ is alkyl, cycloalkyl, benzyl, halobenzyl, alkylbenzyl or haloalkylbenzyl;

each of $R^6$ and $R^7$ is, independently, hydrogen, alkyl, cycloalkyl, alkenyl, alkynyl, alkoxy, phenyl, benzyl, or $SO_2R^8$ or is one of said radicals substituted by halogen, alkyl, or cyano, $R^8$ being the same as $R^6$ other than hydrogen or $SO_2R^8$;

X is hydrogen, halogen, alkyl, haloalkyl, alkoxy, or nitro;

Y is hydrogen, halogen, alkyl, alkoxy, haloalkyl, haloalkylsulfinyl, haloalkoxy, or alkylthio;

NHet is a monovalent nitrogen-containing group of the formula

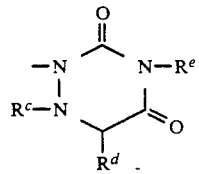

in which $R^c$ and $R^d$ are each H or together constitute a double bond and $R^e$ is alkyl or haloalkyl; and in which any alkyl, alkenyl, alkynyl or alkylene moiety has up to about 6 carbon atoms and any cycloalkyl group has from about 3 to 6 carbon atoms.

2. A compound as in claim 1 in which X is F or Cl, and Y is Cl or Br.

3. A compound as in claim 2 in which Q is $CH_2CH(Cl)Q'$.

4. A compound as in claim 3 in which Q' is $CO_2R^5$ and $R^5$ is lower alkyl.

5. A compound as in claim 4 in which $R^5$ is ethyl.

6. A compound as in claim 1 in which Q is $CH=CHQ'$.

7. A compound as in claim 1 in which Q is $CH_2CH_2Q'$.

8. A compound as in claim 1 in which Q is $CH_2CH(Cl)Q'$.

9. A compound as in claim 2 in which Q is $CH=CHQ'$.

10. A compound as in claim 2 in which Q is $CH_2CH_2Q'$.

11. A herbicidal composition comprising a herbicidally effective amount of the compound of claim 1 in admixture with a suitable carrier.

12. A method for controlling undesired plant growth which comprises applying to the locus where control is desired a herbicidally effective amount of the composition of claim 11.

13. A herbicidal composition comprising a herbicidally effective amount of the compound of claim 2 in admixture with a suitable carrier.

14. A method for controlling undesired plant growth which comprises applying to the locus where control is desired a herbicidally effective amount of the composition of claim 13.

15. A herbicidal composition comprising a herbicidally effective amount of the compound of claim 3 in admixture with a suitable carrier.

16. A method for controlling undesired plant growth growth which comprises applying to the locus where control is desired a herbicidally effective amount of the composition of claim 15.

17. A herbicidal composition comprising an herbicidally effective amount of the compound of claim 4 in admixture with a suitable carrier.

18. A method for controlling undesired plant growth which comprises applying to the locus where control is desired a herbicidally effective amount of the composition of claim 17.

19. A herbicidal composition comprising an herbicidally effective amount of the compound of claim 5 in admixture with a suitable carrier.

20. A method for controlling undesired plant growth which comprises applying to the locus where control is desired a herbicidally effective amount of the composition of claim 19.

21. A herbicidal composition comprising a herbicidally effective amount of the compound of claim 6 in admixture with a suitable carrier.

22. A method for controlling undesired plant growth which comprises applying to the locus where control is desired a herbicidally effective amount of the composition of claim 21.

23. A herbicidal composition comprising a herbicidally effective amount of the compound of claim 7 in admixture with a suitable carrier.

24. A method for controlling undesired plant growth growth which comprises applying to the locus where control is desired a herbicidally effective amount of the composition of claim 23.

25. A herbicidal composition comprising an herbicidally effective amount of the compound of claim 8 in admixture with a suitable carrier.

26. A method for controlling undesired plant growth which comprises applying to the locus where control is desired a herbicidally effective amount of the composition of claim 25.

27. A herbicidal composition comprising an herbicidally effective amount of the compound of claim 9 in admixture with a suitable carrier.

28. A method for controlling undesired plant growth which comprises applying to the locus where control is desired a herbicidally effective amount of the composition of claim 27.

29. A herbicidal composition comprising a herbicidally effective amount of the compound of claim 10 in admixture with a suitable carrier.

30. A method for controlling undesired plant growth which comprises applying to the locus where control is desired a herbicidally effective amount of the composition of claim 29.

* * * * *

UNITED STATES PATENT AND TRADEMARK OFFICE
CERTIFICATE OF CORRECTION

PATENT NO. : 5,035,740

DATED : July 30, 1991

INVENTOR(S) : Kathleen M. Poss

It is certified that error appears in the above-identified patent and that said Letters Patent is hereby corrected as shown below:

Column 11, line 33, "war" should read --warm--. Column 23, line 63, "$CH_2CH(Cl)CO_2CH(CH(CH_3)_2$" should read --$CH_2CH(Cl)CO_2CH(CH_3)2$--. Column 33, line 40, compound no. "30A" should read --40A--.

Signed and Sealed this

Twenty-seventh Day of October, 1992

Attest:

DOUGLAS B. COMER

Attesting Officer     Acting Commissioner of Patents and Trademarks